United States Patent

Bicz

[11] Patent Number: 5,828,627
[45] Date of Patent: Oct. 27, 1998

[54] METHOD OF AND APPARATUS FOR PRODUCING SPHERICAL WAVES IN THE ULTRASONIC RANGE

[75] Inventor: Wieslaw Bicz, Wroclaw, Poland

[73] Assignee: Sonident Anstalt Liechtensteinischen Rechts, Vaduz, Liechtenstein

[21] Appl. No.: 725,351

[22] Filed: Sep. 26, 1996

Related U.S. Application Data

[63] Continuation-in-part of Ser. No. 349,879, Dec. 6, 1994, abandoned.

[30] Foreign Application Priority Data

May 30, 1994 [DE] Germany ............................ 44 18 830.7

[51] Int. Cl.$^6$ ............................. H04R 17/00; G10K 11/08
[52] U.S. Cl. ........................ 367/140; 181/177; 181/192; 73/642; 310/335; 381/154
[58] Field of Search .................................... 367/140, 150, 367/151; 73/642; 310/335; 181/175, 177, 192; 381/154, 155

[56] References Cited

U.S. PATENT DOCUMENTS

| | | | |
|---|---|---|---|
| 1,358,883 | 11/1920 | Seabrook | 181/192 |
| 3,934,460 | 1/1976 | Sherwin et al. | 310/335 |
| 4,320,475 | 3/1982 | Leclerc et al. | 367/149 |
| 4,536,861 | 8/1985 | Graindorge | 367/149 |

FOREIGN PATENT DOCUMENTS

| | | | |
|---|---|---|---|
| 745611 | 5/1933 | France | 310/335 |
| 410 523 | 3/1925 | Germany . | |
| 301185 | 7/1971 | Russian Federation | 310/335 |
| 545924 | 3/1977 | Russian Federation | 73/642 |
| WO 91/05331 | 4/1991 | WIPO . | |

*Primary Examiner*—Harold J. Tudor
*Attorney, Agent, or Firm*—Herbert Dubno

[57] ABSTRACT

A generator for spherical ultrasonic waves can replace a point source transducer and has a large-area transducer whose output ultrasonic waves are condensed in a funnel and fed to a monomodal waveguide, e.g. a tube at the output end of which phase-correct perfectly spherical waves are emitted.

8 Claims, 2 Drawing Sheets

METHOD OF AND APPARATUS FOR PRODUCING SPHERICAL WAVES IN THE ULTRASONIC RANGE

CROSS REFERENCE TO RELATED APPLICATION

This application is a File Wrapper Continuation-in-Part Application of Ser. No. 08/349,879 filed 6 Dec. 1994 now abandoned and is related to the commonly owned application Ser. No. 08/220,712 filed 30 Mar. 1994, now U.S. Pat. No. 5,515,298 issued 7 May 1996.

FIELD OF THE INVENTION

The present invention relates to a method of producing perfect spherical waves in the ultrasonic range and to an apparatus for generating these spherical waves.

BACKGROUND OF THE INVENTION

Ultrasonic waves are used, inter alia, to determine the surface contours of objects or the structuring of objects close to a surface exposed to an ultrasonic surface. In an apparatus utilizing these principles, the object may be placed upon a support exposed to the ultrasonic waves which may be transmitted through a medium capable of wave propagation, e.g. a liquid such as water. One application of the principle is the determination of the ridge pattern of a fingerprint utilizing reflected and back-scattered ultrasonic waves which can be picked up by a multiplicity of transducers as described in the aforementioned copending application or pick-ups which are connected to transducers when a lesser number of transducers are to be used as described in the copending application Ser. No. 08/349,880, filed 6 Dec. 1994 and entitled "Method of and Apparatus for the Detection of an Ultrasonic Field" now U.S. Pat. No. 5,589,636.

It is advantageous in such applications and elsewhere to subject the object to ultrasonic waves which are as close to spherical waves as is possible and in the past these could be achieved only by employing a very small ultrasonic wave generator or transducer (electrical-to-acoustic generator).

It has been found, however, that even with such very small ultrasonic generators, phase-correct waves cannot be produced. The term "phase-correct surface" is intended to refer to waves whose initial wavefront has a perfectly spherical configuration and is followed by successive wavefronts parallel to the first, i.e. of the same spherical character.

A perfect spherical waveform is of importance in all applications in which the phase of the wave is to be measured or evaluated. Practically all ultrasonic devices that operate with reflected and back-scattered ultrasonic waves can be improved by the use of perfect spherical waves even in cases in which the wave form may not be considered of significance.

In many cases, moreover, it is desirable to use ultrasonic waves whose intensity falls off equally on both sides of a symmetry axis, preferably with a gaussian distribution. The gaussian distribution ensures that the intensity in the middle of the wave, i.e. along the symmetry axis, is at a maximum and the amplitude toward the sides is reduced relative to the maximum. Such surfaces have been found to be desirable in applications in which high intensity waves along the boundary of the measured field create perturbations or distortions in the measurements.

OBJECTS OF THE INVENTION

It is, therefore, the principal object of the present invention to provide an improved method of generating spherical ultrasonic waves which does not require an excessively small ultrasonic transducer and therefore can utilize a higher power ultrasonic transducer than has been possible heretofore for the generation of ultrasonic waves.

Another object of this invention is to overcome the drawbacks in earlier systems for producing ultrasonic waves of spherical and phase-correct wave form.

It is also an object of the invention to provide an improved ultrasonic wave generator capable of producing perfectly spherical ultrasonic waves and overcoming drawbacks of prior art systems.

The object of the invention is also to provide an improved method of generating spherical waves and an apparatus for that purpose which can ensure that not only an initial wave front but all subsequent wave fronts which are generated will have a spherical topography.

Still another object of the invention is to provide an ultrasonic wave-generating method and apparatus which produces ultrasonic waves whose intensity falls uniformly to opposite sides of a symmetry axis, preferably with a gaussian distribution.

SUMMARY OP THE INVENTION

These objects and others which will become apparent hereinafter are attained, in accordance with the invention, in a method for generating a perfect spherical wave with a Gaussian intensity distribution which comprises the steps of:

(a) energizing an ultrasonic transducer to produce initial ultrasonic waves which emanate from the transducer;

(b) confining the initial ultrasonic waves emanating from the transducer to condense the initial ultrasonic waves and produce condensed ultrasonic waves;

(c) directing the condensed ultrasonic waves into an end of a monomodal ultrasonic waveguide; and (d) propagating the condensed ultrasonic waves through the monomodal ultrasonic waveguide and emitting from an opposite end of the monomodal waveguide substantially spherical ultrasonic waves into free space at the opposite end.

Preferably the environment through which the initial ultrasonic waves pass is such that the condensation is effected slowly (progressively) and continuously.

A generator of spherical ultrasonic surface, therefore, can comprise:

an ultrasonic transducer producing initial ultrasonic waves which emanate from the transducer;

a funnel positioned to receive the initial ultrasonic waves emanating from the transducer for confining the initial ultrasonic waves emanating from the transducer to condense the initial ultrasonic waves and produce condensed ultrasonic waves; and a monomodal ultrasonic waveguide in the form of a tube having an inlet end connected to the funnel for receiving the condensed ultrasonic waves and, upon propagation of the condensed ultrasonic waves through the monomodal ultrasonic waveguide, emitting from an opposite outlet end of the monomodal waveguide substantially spherical ultrasonic waves into free space. The tube preferably has a diameter of 10 wavelengths of initial ultrasonic waves.

With the invention, an entirely conventional ultrasonic transducer with a relatively large diameter of several millimeters can be used. The waves which are generated by such a transducer are not homogeneous and thus these waves differ from planar waves or spherical waves very significantly with respect to their distribution in space and in time both with respect to amplitude and phase. By providing a funnel to condense the nonhomogeneous waves of the transducer and providing a tube at the end of that funnel to act as a monomodal waveguide, I can transform the nonhomogeneous waves into perfect spherical waves.

The tube can have a diameter of about ten wavelengths of the ultrasonic waves.

The funnel is preferably so shaped and positioned that the total wave energy is fed to the tube, the output end of the tube forming in effect a point source for the spherical wave which is perfectly phase-correct, i.e. is a perfect spherical wave, and which also has the desired gaussian intensity distribution. A perfect spherical wave is an ultrasonic wave in which each wave front has the configuration of a segment of a sphere emanating from the same point.

With the invention, it is possible to utilize a large generator with a high energy output which can be significantly greater than that of a conventional point source.

The funnel and the tube of the invention can be composed of a solid body and it has been found that a sound-absorbing material, preferably a plastic, can be especially suitable. The funnel and tube can be disposed in a liquid bath or in a gas atmosphere. It has also been found to be possible to provide the funnel and tube so that they are externally surrounded by a solid body and/or can internally contain a solid body as an ultrasound transmitting medium. The length of the tube serving as the waveguide should, of course, be sufficient to enable the emitted ultrasound to have the perfect spherical waveform as required. The tube can be optionally bent so that the starting point of the spherical wave can be placed wherever necessary or desired.

It is also possible to provide instead of a tube some other waveguide such as a glass fiber at the outlet of the funnel. The ultrasonic transducer has a frequency range with a minimum of 2 MHz and generates perfectly spherical waves over this range. Best results are obtained in a frequency range of 2 MHz to 50 MHz with a preferred range being 2 MHz to 12 MHz and a highly advantageous range being 2 MHz to 10 MHz.

BRIEF DESCRIPTION OF THE DRAWING

The above and other objects, features, and advantages will become more readily apparent from the following description, reference being made to the accompanying drawing in which.

SPECIFIC DESCRIPTION

Figure 1:
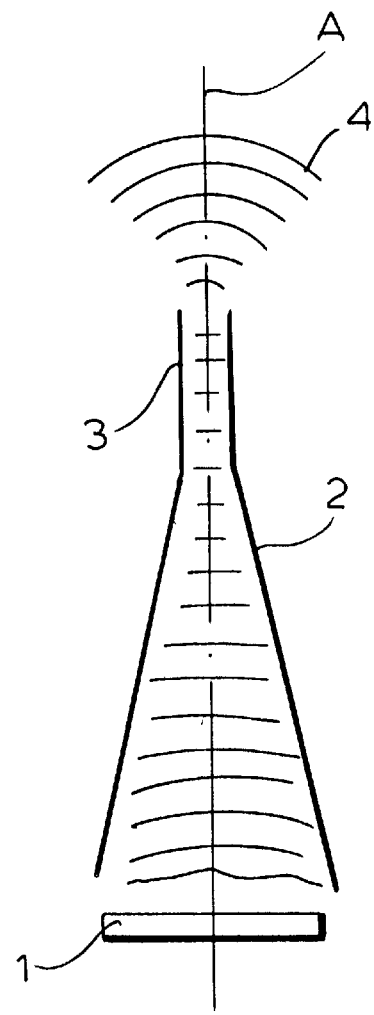
FIG. 1 is a cross sectional view in highly diagrammatic form illustrating an apparatus for producing spherical waves in accordance with the invention.

As can be seen from FIG. 1, an ultrasonic transducer 1, which can be substantially larger than point sources hitherto thought to be necessary for the generation of a spherical surface, is provided at the wide side of a funnel 2 which condenses these waves progressively and slowly as they are propagated through the funnel. At the outlet end of the funnel, a tube 3 is provided and forms a monomodal waveguide from which the ultrasonic waves 4 emerge in phase-correct relationship and with a spherical wavefront.

Figure 2:
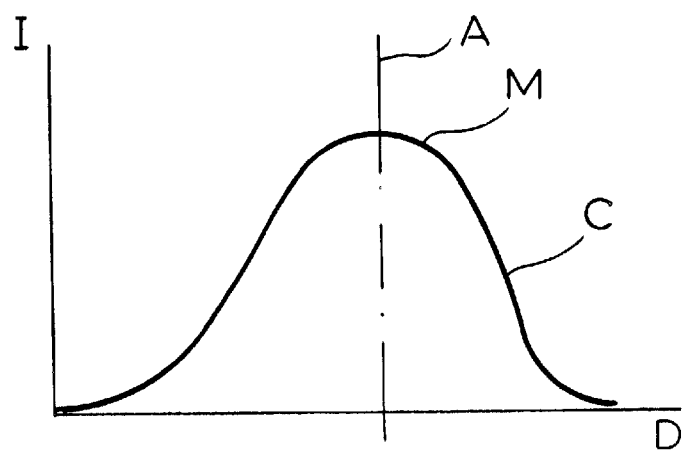
FIG. 2 is a graph showing the gaussian intensity distribution of these waves.

The waves provide a field whose intensity falls off to either side of the axis of symmetry A in accordance with a gaussian curve C with a maximum along the symmetry axis in a graph in which intensity is plotted versus distance as shown in FIG. 2.

Figure 3:
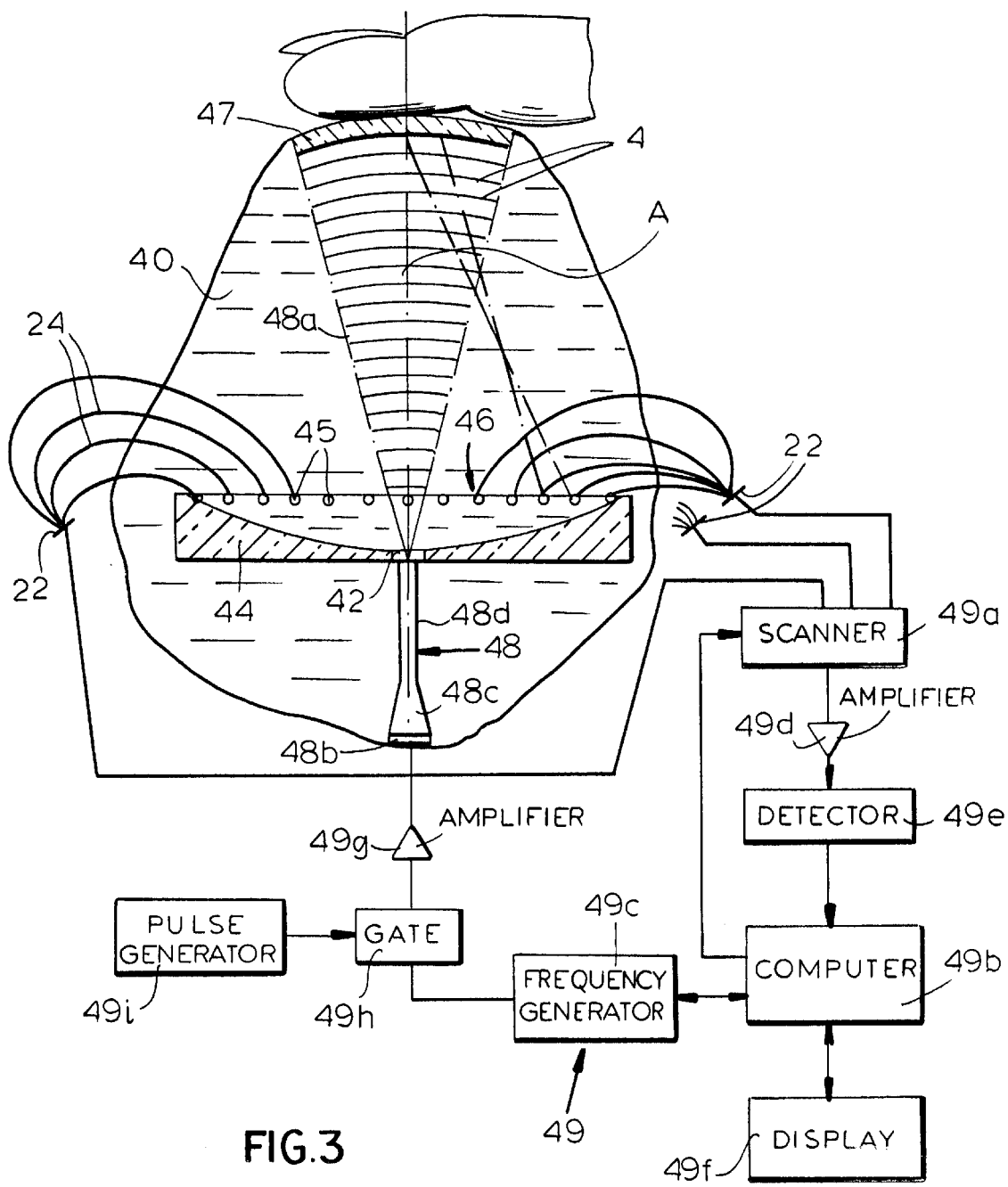
FIG. 3 shows an application of the spherical wave generator of the invention.

The spherical ultrasonic wave generator of FIG. 1 can be utilized in an apparatus of the type shown in FIG. 3 which can be employed, for example, for ascertaining the fingerprint of an individual in accordance with the principles of Ser. No. 08/220,112 but wherein the individual pick-up transducers thereof are replaced by the ultrasonic pick ups and waveguides described in the copending application Ser. No. 08/349,880 filed 6 Dec. 1994.

The apparatus here comprises an ultrasonic generator made up of a transducer 48b whose ultrasonic output is condensed in the funnel 48c communicating with the waveguide tube 48d of the ultrasonic generator 48 so that at a hole 42 of a carrier 44, ultrasonic waves 4 are propagated through the liquid medium, e.g. water, in such manner that a cone 48a of the waves is radiated toward a support 47. The entire area of the support 47 is irradiated by these perfectly spherical waves.

The body of liquid 40 forms the sound-transmitting medium between the ultrasonic source 48 and support 47 (see U.S. Pat. No. 5,258,422). The carrier 44 has a spherical surface 43. The support 47, which is transmissive to ultrasonic waves and can be composed of glass is a convex-concave disk of constant wall thickness, the convex side of which serves as a resting surface for the object, namely, the tip of the finger when the apparatus is used to determine the contours of the finger, i.e. the fingerprint.

On the surface of the carrier 44, instead of individual transducers as provided in Ser. No. 08/220,712, which also may be used here, numerous small receiving collectors 45 are provided as described in Ser. No. 08/349,880 filed 6 Dec. 1994, closely adjacent one another in a receiving collector ring or annular array 46. The surface 43 is preferably spherical.

The collectors 45 can be provided with waveguides connected to respective transducers 22 as described in the last-mentioned copending application and the transducers 22 may be connected, in turn, to a scanner 49a of the circuitry 49.

The individual transducers 22 are scanned in succession by the scanner 49a under the control of the computer 49b which can also receive an input from the frequency generator 49c so that with each change in frequency, the receiving transducers can be scanned in sequence.

The scanned output is amplified at 49d to feed the detector 49e whose signal is supplied to the computer 49b and provides a display at 49f of the pattern of the fingerprint or some property thereof. The frequency generator 49c can supply an amplifier 49g through a gate 49h feeding the transducer 48b. The gate 49h is triggered from a pulse-generator or other pulse source 49i. The apparatus, therefore, operates in the manner described in copending application Ser. No. 08/220,712 to determine the contours of the object on the support 47.

I claim:

1. A method of generating spherical ultrasonic waves, comprising the steps of:
   (a) energizing an ultrasonic transducer to produce initial ultrasonic waves of an ultrasonic frequency which emanate from said transducer;
   (b) confining the initial ultrasonic waves emanating from said transducer by passing the ultrasonic waves through a frustoconical funnel with straight-line generatrices and free from a solid filling to condense the initial ultrasonic waves and produce condensed ultrasonic waves;

(c) directing said condensed ultrasonic waves into an end of a monomodal ultrasonic waveguide in the form of a tube free from a solid filling of constant cross section, traversed by the condensed ultrasonic waves with a diameter greater than the wavelength of the ultrasonic waves; and (d) propagating said condensed ultrasonic waves through said monomodal ultrasonic waveguide and emitting from an opposite end of said monomodal waveguide substantially spherical ultrasonic waves into free space at said opposite end.

2. The method defined in claim 1 wherein said initial ultrasonic waves are condensed in step (b) slowly and continuously.

3. A generator of spherical waves ultrasonic waves, comprising:

an ultrasonic transducer producing initial ultrasonic waves of an ultrasonic frequency which emanate from said transducer;

a frustoconical funnel with straight-line generatrices and free from a solid filling positioned to receive said initial ultrasonic waves emanating from said transducer for confining the initial ultrasonic waves emanating from said transducer to condense the initial ultrasonic waves and produce condensed ultrasonic waves; and a monomodal ultrasonic waveguide in the form of a tube free from a solid filling of constant cross section, traversed by the condensed ultrasonic waves with a diameter greater than the wavelength of said ultrasonic waves, said tube having an inlet end connected to said funnel for receiving said condensed ultrasonic waves and, upon propagation of said condensed ultrasonic waves through said monomodal ultrasonic waveguide, emitting from an opposite outlet end of said monomodal waveguide substantially spherical ultrasonic waves into free space.

4. The generator defined in claim 3 wherein said tube has an inner diameter of 10 wavelengths of initial ultrasonic waves.

5. A method of generating spherical ultrasonic waves, comprising the steps of:

(a) energizing an ultrasonic transducer to produce initial ultrasonic waves of an ultrasonic frequency of at least 2 MHz which emanate from said transducer;

(b) confining the initial ultrasonic waves emanating from said transducer by passing the ultrasonic waves through a frustoconical funnel with straight-line generatrices and free from a solid filling to condense the initial ultrasonic waves and produce condensed ultrasonic waves;

(c) directing said condensed ultrasonic waves into an end of a monomodal ultrasonic waveguide in the form of a tube free from a solid filling of constant cross section, traversed by the condensed ultrasonic waves with a diameter greater than the wavelength of the ultrasonic waves; and (d) propagating said condensed ultrasonic waves through said monomodal ultrasonic waveguide and emitting from an opposite end of said monomodal waveguide substantially spherical ultrasonic waves into free space at said opposite end.

6. The method defined in claim 5 wherein said initial ultrasonic waves are condensed in step (b) slowly and continuously.

7. A generator of spherical waves ultrasonic waves, comprising:

an ultrasonic transducer producing initial ultrasonic waves of an ultrasonic frequency of at least 2 MHz which emanate from said transducer;

a frustoconical funnel with straight-line generatrices and free from a solid filling positioned to receive said initial ultrasonic waves emanating from said transducer for confining the initial ultrasonic waves emanating from said transducer to condense the initial ultrasonic waves and produce condensed ultrasonic waves; and a monomodal ultrasonic waveguide in the form of a tube free from a solid filling of constant cross section, traversed by the condensed ultrasonic waves with a diameter greater than the wavelength of said ultrasonic waves, said tube having an inlet end connected to said funnel for receiving said condensed ultrasonic waves and, upon propagation of said condensed ultrasonic waves through said monomodal ultrasonic waveguide, emitting from an opposite outlet end of said monomodal waveguide substantially spherical ultrasonic waves into free space.

8. The generator defined in claim 7 wherein said tube has an inner diameter of 10 wavelengths of initial ultrasonic waves.

* * * * *